US010702255B1

(12) United States Patent
Desai et al.

(10) Patent No.: US 10,702,255 B1
(45) Date of Patent: Jul. 7, 2020

(54) SPECIMEN RETRIEVAL SYSTEM

(71) Applicant: DeRoyal Industries, Inc., Powell, TN (US)

(72) Inventors: Dhanvin Desai, Knoxville, TN (US); Scott Barnes, Knoxville, TN (US); Lee Freeman, Knoxville, TN (US); Mike Kastura, Knoxville, TN (US); Ethan Edward Valentine, Knoxville, TN (US)

(73) Assignee: DEROYAL INDUSTRIES, INC., Powell, TN (US)

( * ) Notice: Subject to any disclaimer, the term of this patent is extended or adjusted under 35 U.S.C. 154(b) by 142 days.

(21) Appl. No.: 16/012,914

(22) Filed: Jun. 20, 2018

Related U.S. Application Data

(63) Continuation-in-part of application No. 15/495,467, filed on Apr. 24, 2017, now Pat. No. 10,420,571.

(51) Int. Cl.
*A61B 17/00* (2006.01)

(52) U.S. Cl.
CPC .............. *A61B 17/00234* (2013.01); *A61B 2017/00287* (2013.01)

(58) Field of Classification Search
CPC ........... A61B 2017/00287; A61B 2017/00867; A61B 2017/2212; A61B 2017/2918; A61B 2017/2924; A61B 2017/2927; A61B 2017/00336; A61B 2017/294; A61B 2017/2946; A61B 17/00234; A61B 17/221; A61B 17/30; A61B 17/00; A61B 17/0293; A61B 17/32056; A61B 10/04; A61F 2002/2484; A61F 2/2481; A61M 1/008
See application file for complete search history.

(56) References Cited

U.S. PATENT DOCUMENTS

| 5,403,324 | A | 4/1995 | Ciervo et al. |
| 6,409,733 | B1 | 6/2002 | Conlon et al. |
| 8,075,567 | B2 | 12/2011 | Taylor et al. |
| 8,425,533 | B2 | 4/2013 | Parihar et al. |
| 8,827,968 | B2 | 9/2014 | Taylor et al. |
| 8,870,894 | B2 | 10/2014 | Taylor et al. |
| D731,052 | S | 6/2015 | Doerr et al. |
| 2007/0073251 | A1 | 3/2007 | Zhou et al. |
| 2009/0182292 | A1* | 7/2009 | Egle ................. A61B 17/00234 604/327 |
| 2011/0184433 | A1 | 7/2011 | Parihar et al. |
| 2013/0023895 | A1 | 1/2013 | Saleh |

OTHER PUBLICATIONS

Espiner Medical Ltd., Master E-Sac, EcoSac, Standard E-Sac, Super E-Sac,The dates of this publication is know known, but it is requested that it be considered as prior art for purposes of examination.
Genicon, Winter Park, Florida U.S.A., Genistrong Specimen Retrieval Bag,The dates of this publication is not known, but it is requested that it be considered as prior art for purposes of examination.
International Searching Authority, International Search Report and Written OpinionPCT/US2017/030416 dated Jul. 19, 2017.

\* cited by examiner

*Primary Examiner* — Elizabeth Houston
*Assistant Examiner* — Mohamed G Gabr
(74) *Attorney, Agent, or Firm* — Luedeka Neely Group, PC

(57) ABSTRACT

A specimen retrieval system of simplified construction. The system is configured for use during laparoscopic surgery to assist in the retrieval and removal of tissue.

8 Claims, 18 Drawing Sheets

SPECIMEN RETRIEVAL SYSTEM

CROSS-REFERENCE TO RELATED APPLICATION

This application is a continuation-in-part of co-pending U.S. application Ser. No. 15/495,467 filed on Apr. 24, 2017, entitled SPECIMEN RETRIEVAL SYSTEM, incorporated herein by reference in its entirety.

FIELD

The present disclosure relates to a medical specimen retrieval system. More particularly, the disclosure relates to a specimen retrieval system for use in laparoscopic surgery.

BACKGROUND

Improvement is desired in the construction of medical specimen retrieval devices of the type utilizing a specimen bag for retrieving tissue specimens during laproscopic surgery.

In particular, what is desired is a retrieval system of simplified construction.

The disclosure advantageously provides a specimen retrieval system for use during laparoscopic surgery to assist in the retrieval and removal of tissue.

SUMMARY

The disclosure relates to specimen retrieval systems.

In one aspect, the specimen retrieval system includes a bag having a flexible basket with an opening configured to be deployable for receiving a tissue specimen, and an elongate string encircling the flexible basket and extending therefrom to terminate remote from the flexible basket, the string being operable to close the opening of the flexible basket. An outer cannula is provided having a distal end and a proximal end with a cannula handle located at the proximal end of the outer cannula, the outer cannula configured to receive the bag therein and to permit passage of the bag through the distal end of the outer cannula for deployment of the bag. The outer cannula further includes an elongate slit adjacent the distal end of the outer cannula configured for enabling positioning of the flexible basket through the slit and for retrieval of the flexible basket through the slit for positioning of the bag within the outer cannula. An interior tube is provided having a distal end slidably positionable within the outer cannula via the proximal end of the outer cannula, the interior tube having a tube handle mounted to a proximal end of the interior tube at a location exterior of the cannula handle. A distal aperture is defined on the interior tube adjacent the distal end of the interior tube and a proximal aperture defined on the interior tube adjacent the proximal end of the interior tube. The distal and proximal apertures are configured for passage of the string into the interior tube via the distal aperture and for passage of the string out of the interior tube via the proximal aperture. A spring secured within the distal end of the interior tube and extending outwardly of the distal end of the interior tube, the spring connectable to the opening of the basket of the bag In another aspect, a specimen retrieval system includes a bag having a flexible basket with an opening configured to be deployable for receiving a tissue specimen, and an elongate string encircling the flexible basket and extending therefrom to terminate remote from the flexible basket, the string being operable to close the opening of the flexible basket. An outer cannula is provided having a distal end and a proximal end with a cannula handle located at the proximal end of the outer cannula, the outer cannula configured to receive the bag therein and to permit passage of the bag through the distal end of the outer cannula for deployment of the bag. An interior tube is provided, having a distal end slidably positionable within the outer cannula via the proximal end of the outer cannula. The interior tube has a tube handle mounted to a proximal end of the interior tube at a location exterior of the cannula handle. A distal aperture is defined on the interior tube adjacent the distal end of the interior tube and a proximal aperture defined on the interior tube adjacent the proximal end of the interior tube. The distal and proximal apertures are configured for passage of the string into the interior tube via the distal aperture and for passage of the string out of the interior tube via the proximal aperture. A spring is secured within the distal end of the interior tube and extending outwardly of the distal end of the interior tube, the spring connectable to the opening of the basket of the bag.

In yet another aspect, a specimen retrieval system includes a bag having a flexible basket with an opening configured to be deployable for receiving a tissue specimen, and an elongate string encircling the flexible basket and extending therefrom to terminate remote from the flexible basket, the string being operable to close the opening of the flexible basket. An outer cannula is provided having a distal end and a proximal end with a cannula handle located at the proximal end of the outer cannula, the outer cannula configured to receive the bag therein and to permit passage of the bag through the distal end of the outer cannula for deployment of the bag. The outer cannula further includes an elongate slit adjacent the distal end of the outer cannula configured for enabling positioning of the flexible basket through the slit and for retrieval of the flexible basket through the slit for positioning of the flexible basket within the outer cannula. An interior tube is provided having a distal end slidably positionable within the outer cannula via the proximal end of the outer cannula. The interior tube has a tube handle mounted to a proximal end of the interior tube at a location exterior of the cannula handle, and a spring secured within the distal end of the interior tube and extending outwardly of the distal end of the interior tube, the spring connectable to the opening of the basket of the bag.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
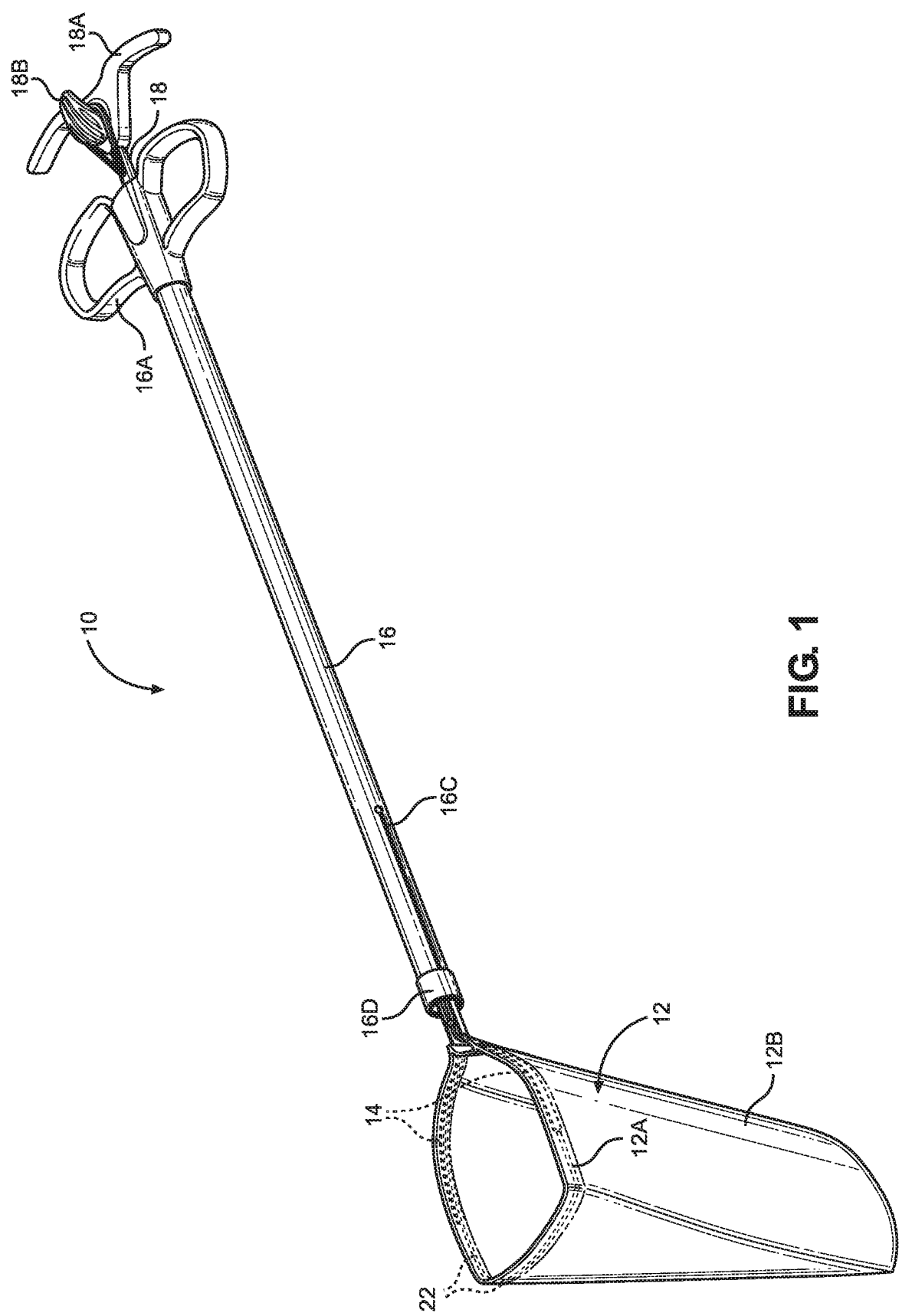
FIG. 1 is a perspective view of a specimen retrieval system according to the disclosure as deployed for retrieving a sample in a surgical procedure.

With reference to the drawings, the disclosure relates to a specimen retrieval system 10 for use during laparoscopic surgery to assist in the retrieval of compromised tissue. The retrieval system is configured to be used with a trocar system and includes a specimen bag 12, springs 14, an outer cannula 16 with a handle 16a configured to provide a pair of rings, an interior tube 18 with a handle 18a, a seal such as gasket or O-ring 20 (FIG. 15), and a string 22 configured for closing of the bag 12.

In general overview, laproscopic surgery typically involves forming three or more incisions. Small tubes or trocars, illustrated as trocar cannula TC in FIGS. 6-9, are placed through these incisions and into the abdomen. Carbon dioxide gas is used to inflate the abdomen and a camera attached to a thin metal telescope or laparoscope is used to view the surgical site. Laproscopic instruments are passed through one or more of the trocars to perform the surgical procedure. take the place of the surgeon's hands and traditional surgical instruments. As part of this, care is taken so that all tissue cut during the procedure, including any tissue of interest (the specimen) is removed from the patient.

The specimen retrieval system 10 according to the disclosure is used in this capacity to remove tissue from the surgical site. Thus, the system 10 utilizes the bag 12 configured to be passed through a trocar, expanded within the surgical site, then retracted and removed via the trocar, all the while containing all tissue and fluids collected in the bag. In many cases, the bag 12 is deployed and retrieved multiple times during a surgical procedure.

Figure 3:
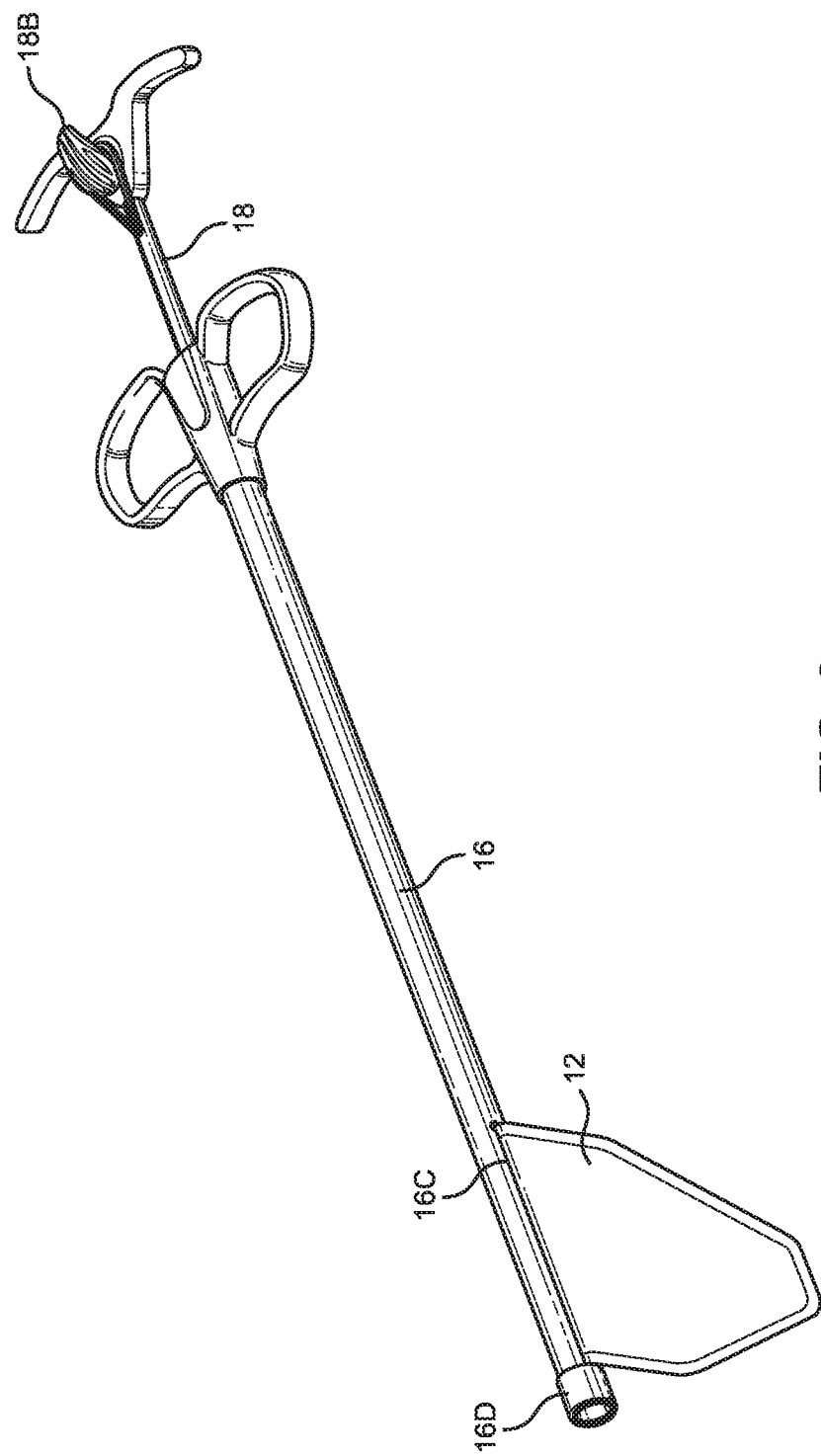
FIG. 3 shows the system as initially configured showing the orientation of a bag component prior to use of the system in a surgical procedure.
Figure 4:
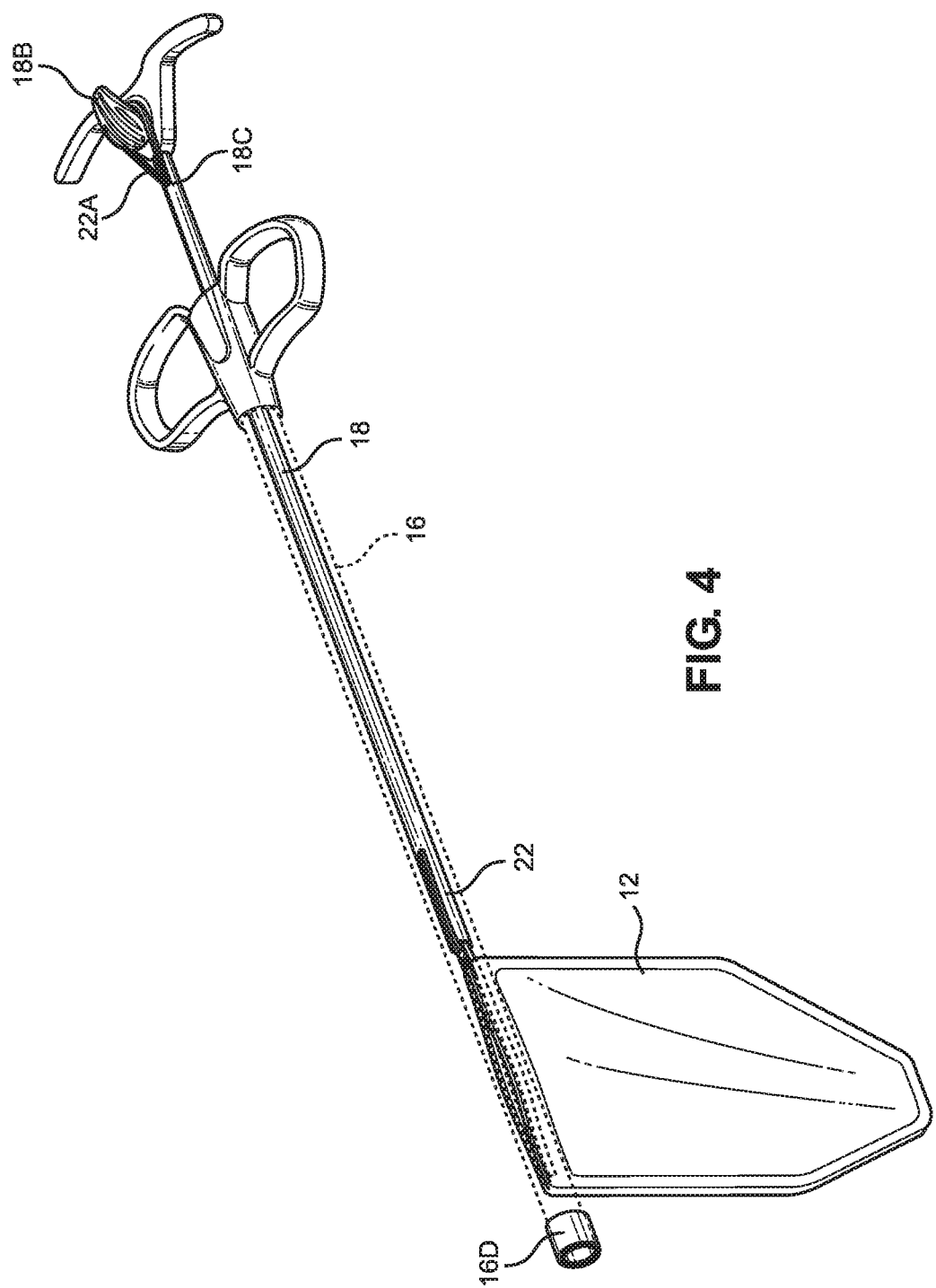
FIG. 4 is the same as FIG. 3, but with an outer cannula thereof transparent.
Figure 5:
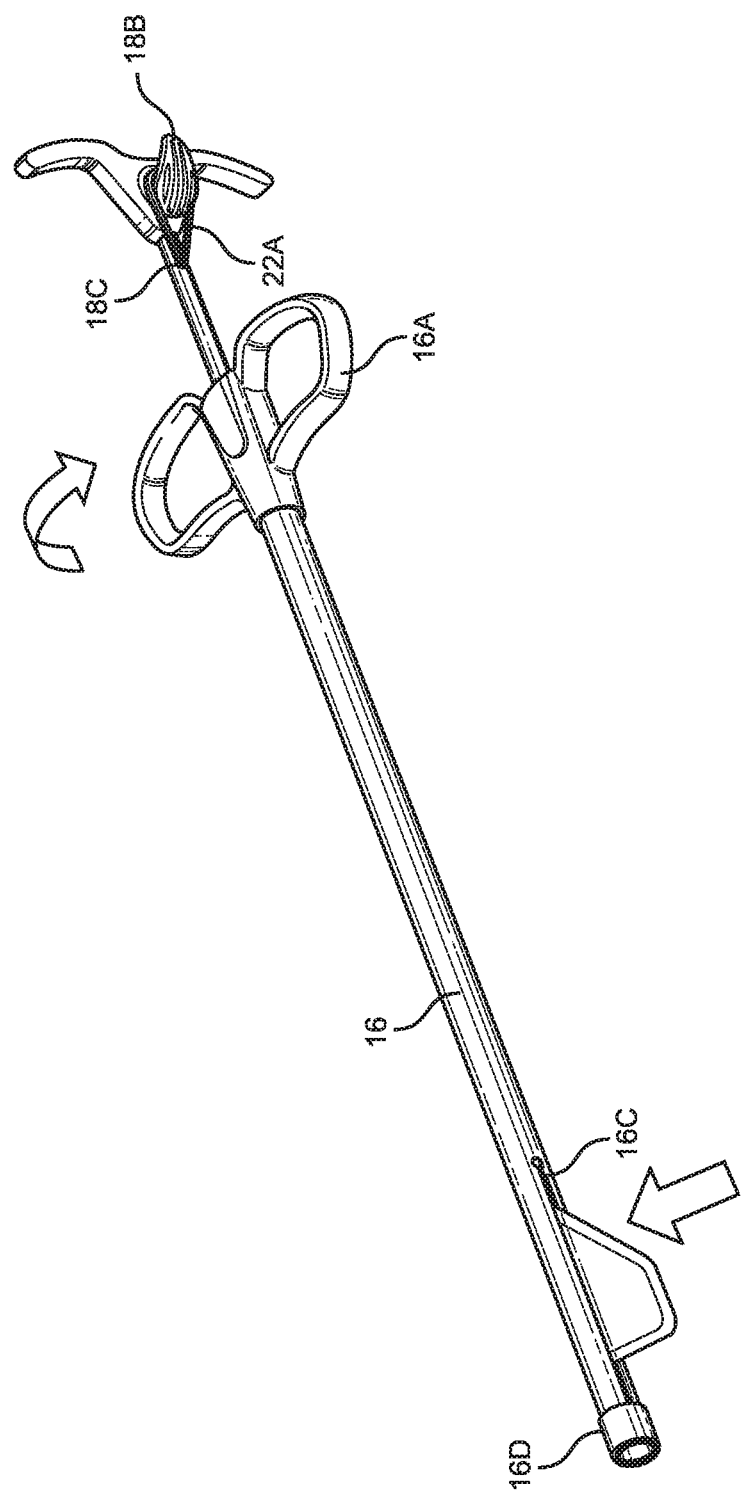
FIG. 5 illustrates retraction of the bag component to prepare the system for deployment inside a patient during a surgical procedure.
Figure 6:
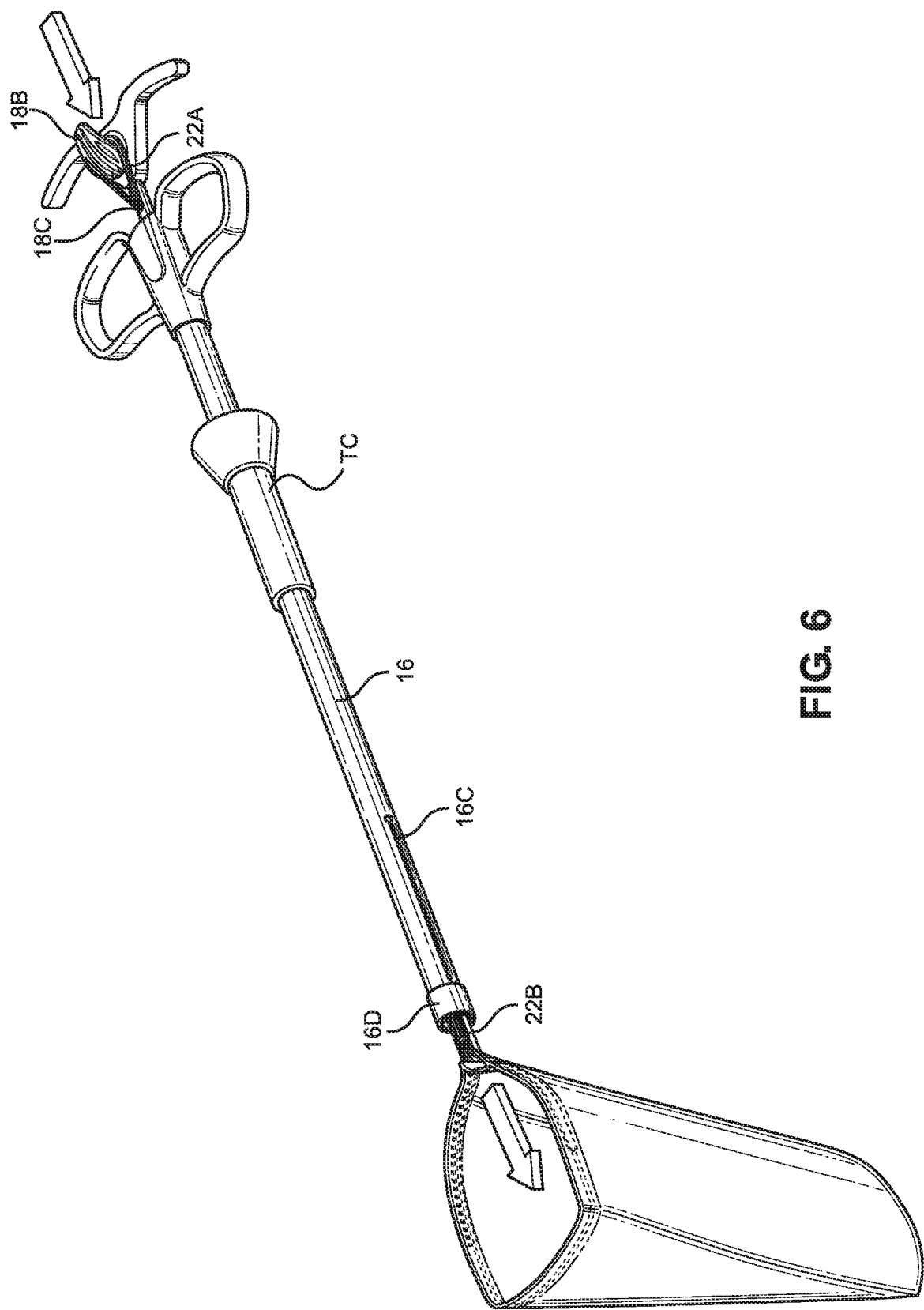
FIG. 6 illustrates deployment of the bag component during a surgical procedure to retrieve a specimen.

FIG. 1 shows the retrieval system as deployed for retrieving a sample in a surgical procedure. Initially, the system 10 is provided to the surgeon as shown in FIGS. 3 and 4, with the bag 12 outside the outer cannula 16 to prevent bending or rolling of the bag to avoid having memory in the material of the bag 12. For use, as shown in FIG. 5, the bag 12 is retracted inside the outer cannula 16 before being inserted through the trocar cannula TC. FIG. 6 shows the bag 12 deployed through the trocar cannula TC for collection of a specimen.

Figure 7:
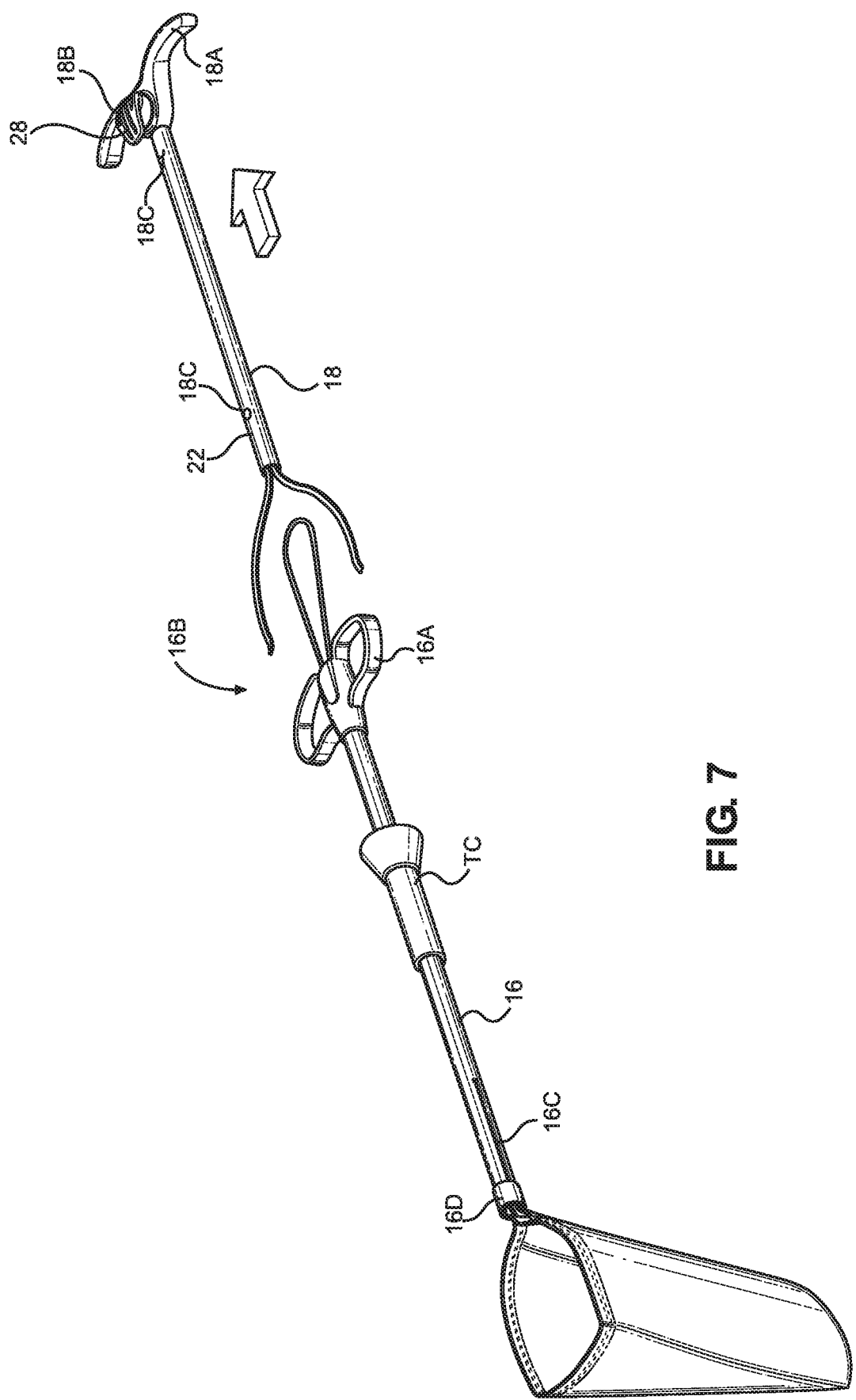
FIGS. 7-9 depict steps in the retrieval of the bag component after use to retrieve a specimen.
Figure 8:
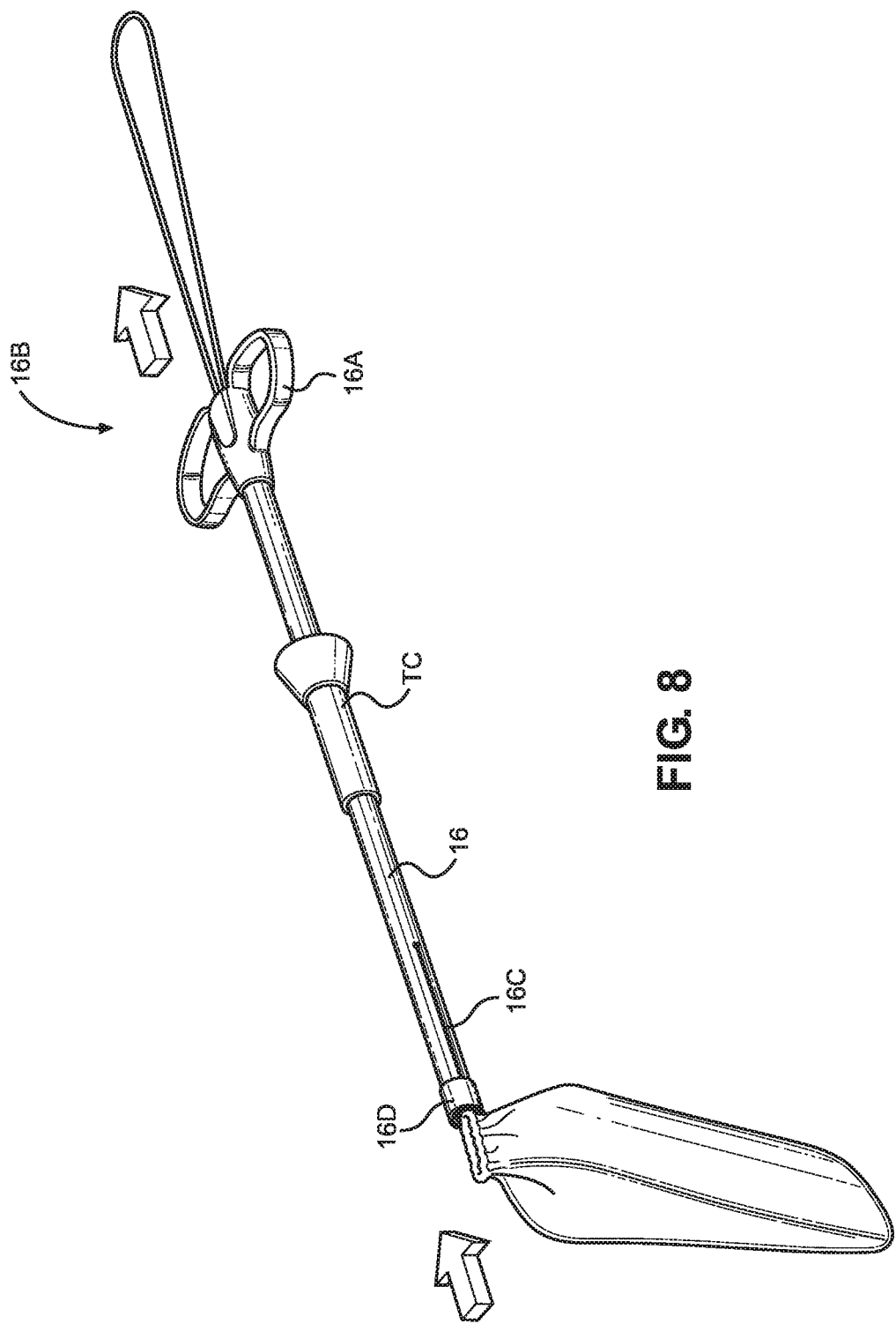
Figure 9:
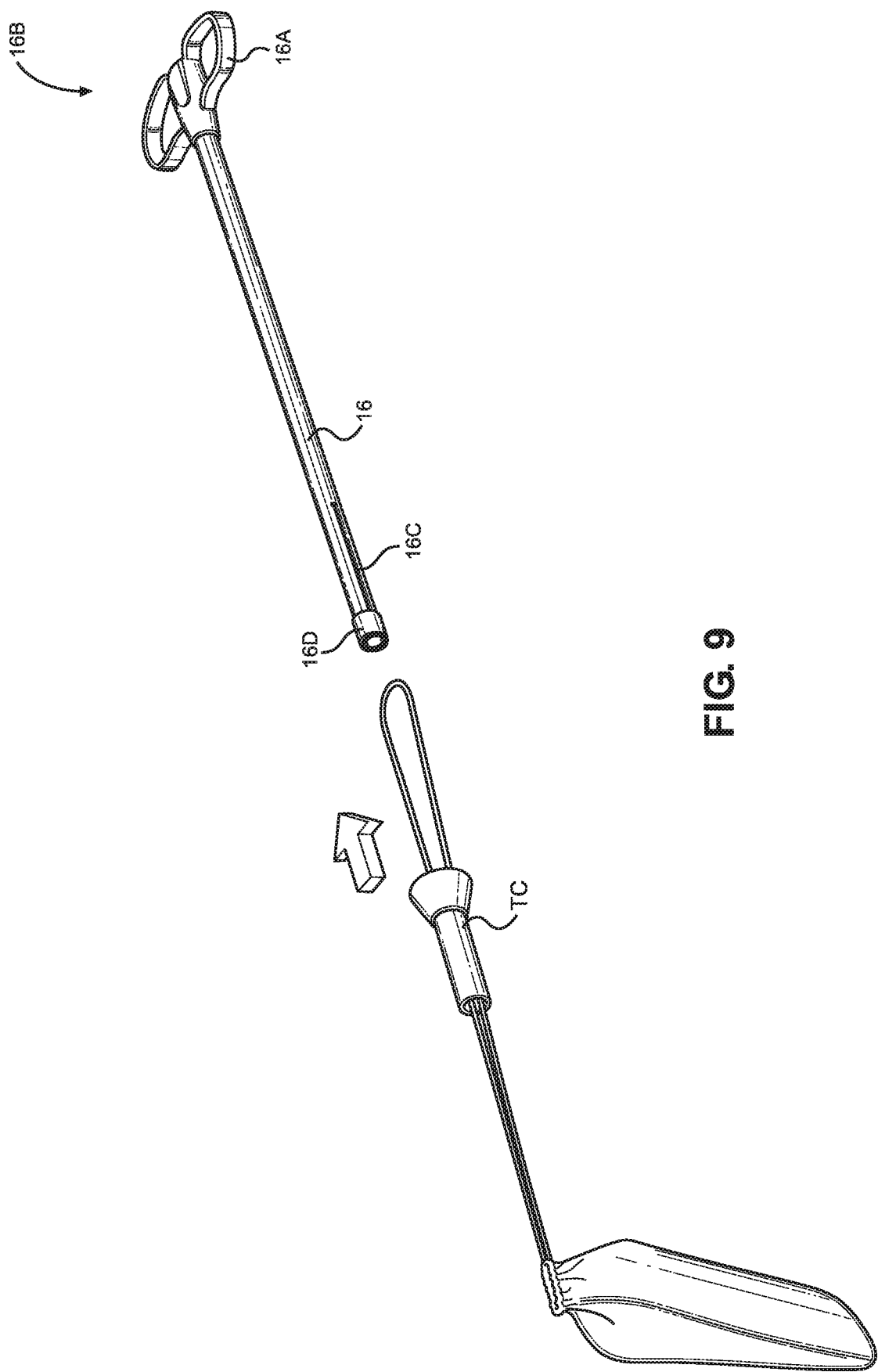

During use of the retrieval system 10, tissue from the surgical procedure is dropped or otherwise deposited inside the bag 12, then the bag 12 and tissue are retrieved simultaneously. The bag 12 is desirably made from a durable material and configured to hold a seal to prevent any parts of the compromised tissue spilling back into the patient. FIGS. 7-9 depict retrieval of the bag 12.

The bag 12 is configured to provide a flexible basket structure and may be made with a translucent rip stop nylon material with a polyurethane inner lining. The rip stop nylon provides durability while the polyurethane allows the bag 12 to be radio frequency welded or heat sealed. The bag 12 is also made to be translucent so the general shape of the tissue can be visualized while still in the bag 12. The bag 12 includes a chase 12a located and extending around the upper perimeter of the bag 12. The chase 12a is sized and configured for receiving the springs 14 and the string 22. The bag 12 defines a flexible basket 12b configured for receiving tissue, specimens and the like.

The springs 14 are utilized to deploy or expand the bag 12 into a configuration within the surgical site suitable for collection of tissue. The springs 14 are preferably flat springs and may be made of metal and are operable to assist in keeping the bag 12 open once deployed. The springs 14 are mounted to the distal end of the interior tube 18 to maintain the springs 14 in a fixed position. Rotation of the interior tube 18 enables the user to rotate the bag 12 once deployed for proper positioning of the bag 12. The distal ends of the springs 14 are located on opposite sides of the chase 12a of the basket 12b of the bag 12 to maintain the basket 12b in an open orientation when deployed, such as shown in FIGS. 1 and 6. A single spring could be utilized to maintain the opening of the basket open, or to be open in a non-circular orientation. However, the use of the pair of springs 14 is preferred.

Figure 14:
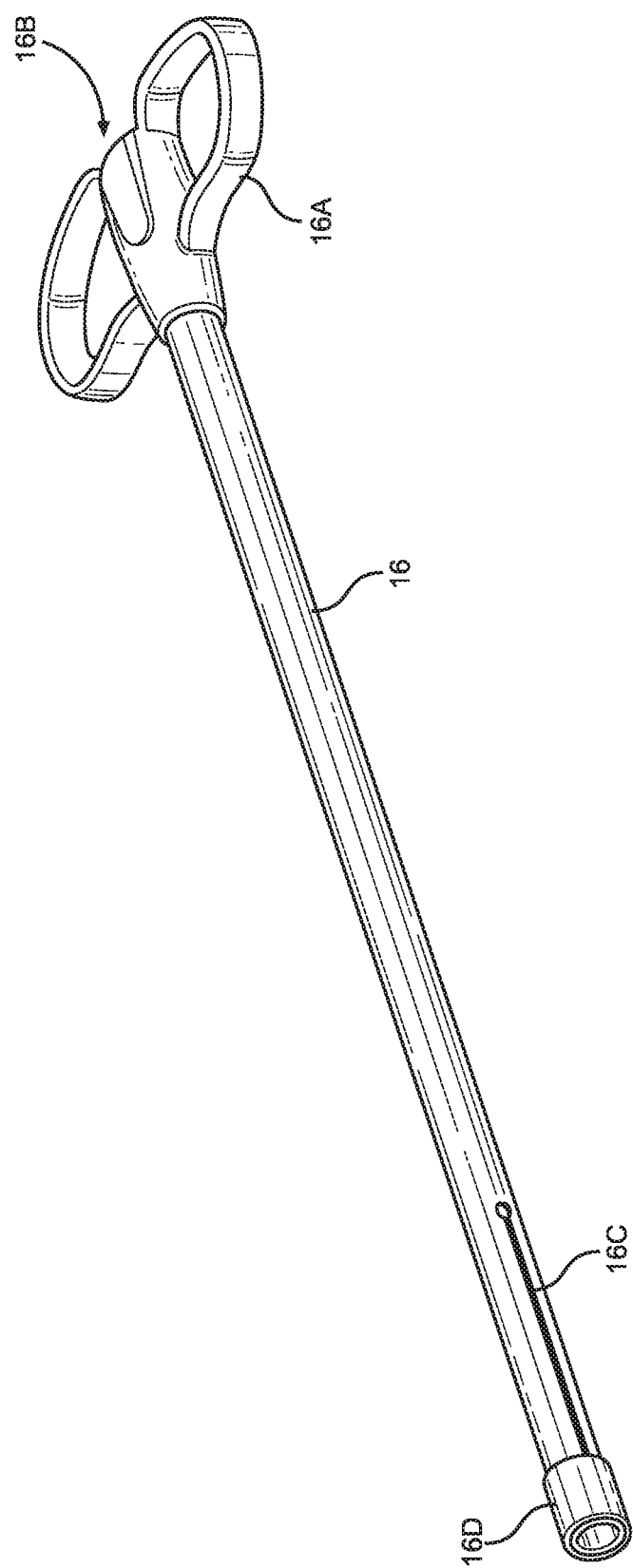
FIG. 14 shows the outer cannula component.

The outer cannula 16 is configured to enable the basket 12b to be deployed therefrom and retracted therein, with the springs 14 yielding to enable the basket 12b to be withdrawing into the cannula 16. In this regard, it is noted that the bag 12 with the interior tube 18 typically does not fit through the trocar by themselves as the working area is very small. Accordingly, the outer cannula 16 with the handle 16a advantageously enables the bag 12 to be retracted when inserting the instrument through the trocar. In addition, the handle 16a is configured to provide an aperture 16b of the same size as the interior of the outer cannula 16 to permit the interior tube 18 to be inserted into the cannula 16 (FIG. 14).

The outer cannula 16 includes an elongate slit 16c proximate the distal end of the cannula 16. The slit 16d is provided as a passage through the sidewall of the cannula 16 so that the bag 12 may initially be located outside the outer cannula 16 as shown in FIGS. 3 and 4 to prevent bending or rolling of the bag to avoid having memory in the material of the bag 12. A cylindrical sleeve 16d is located at the distal end of the outer cannula 16 to close the distal end of the slit 16c to that the bag 12 does not engage the slit 16c when the bag 12 is being retracted back into the outer cannula 16. The slit could be formed so as to not extend to the end of the cannula 16 and avoid the need for the sleeve 16d. However, it is easier to form the slit 16c in the shown manner.

Figure 15:
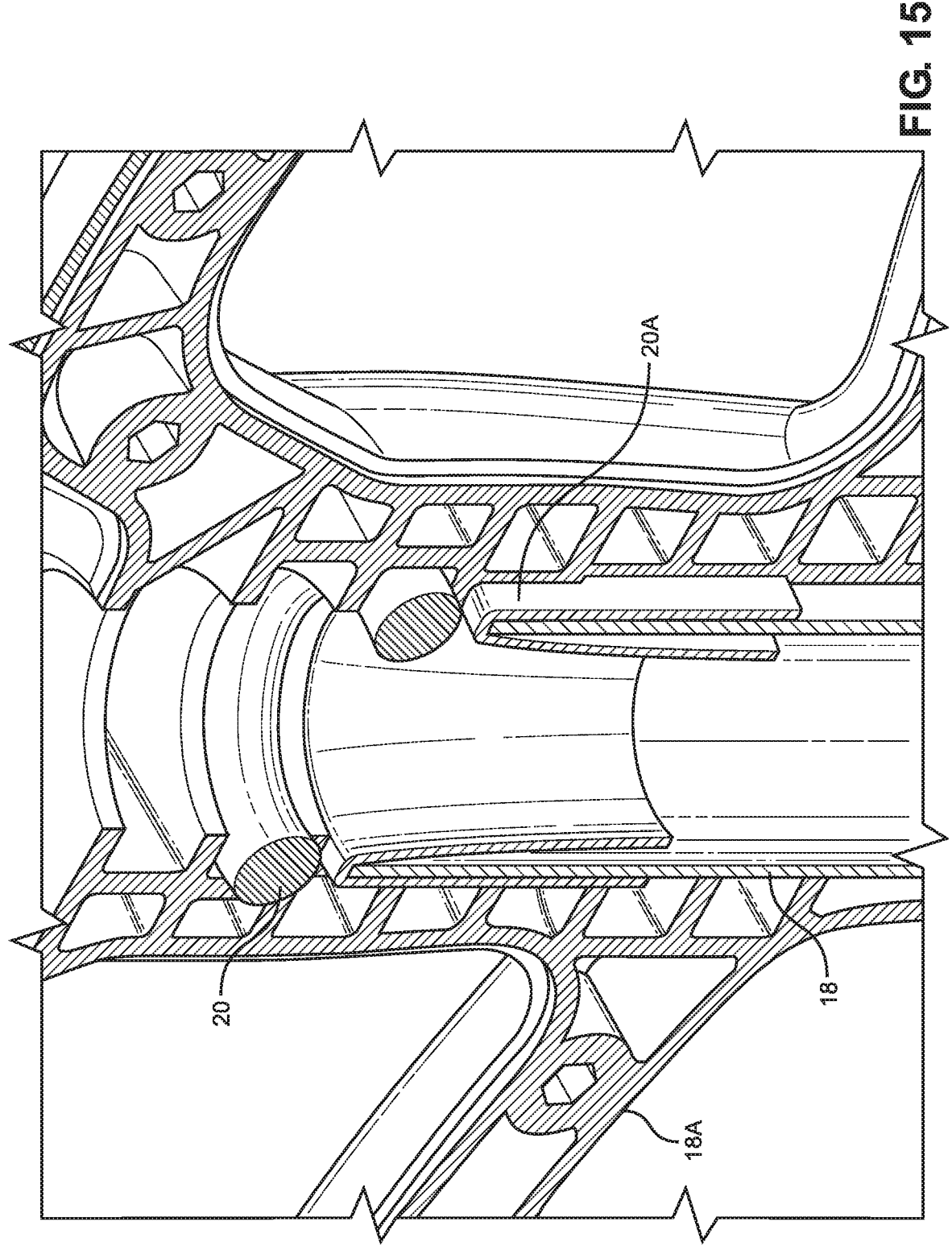
FIG. 15 shows an O-ring disposed within a handle of the outer cannula for preventing escape of procedure inflation gas.
Figure 16:
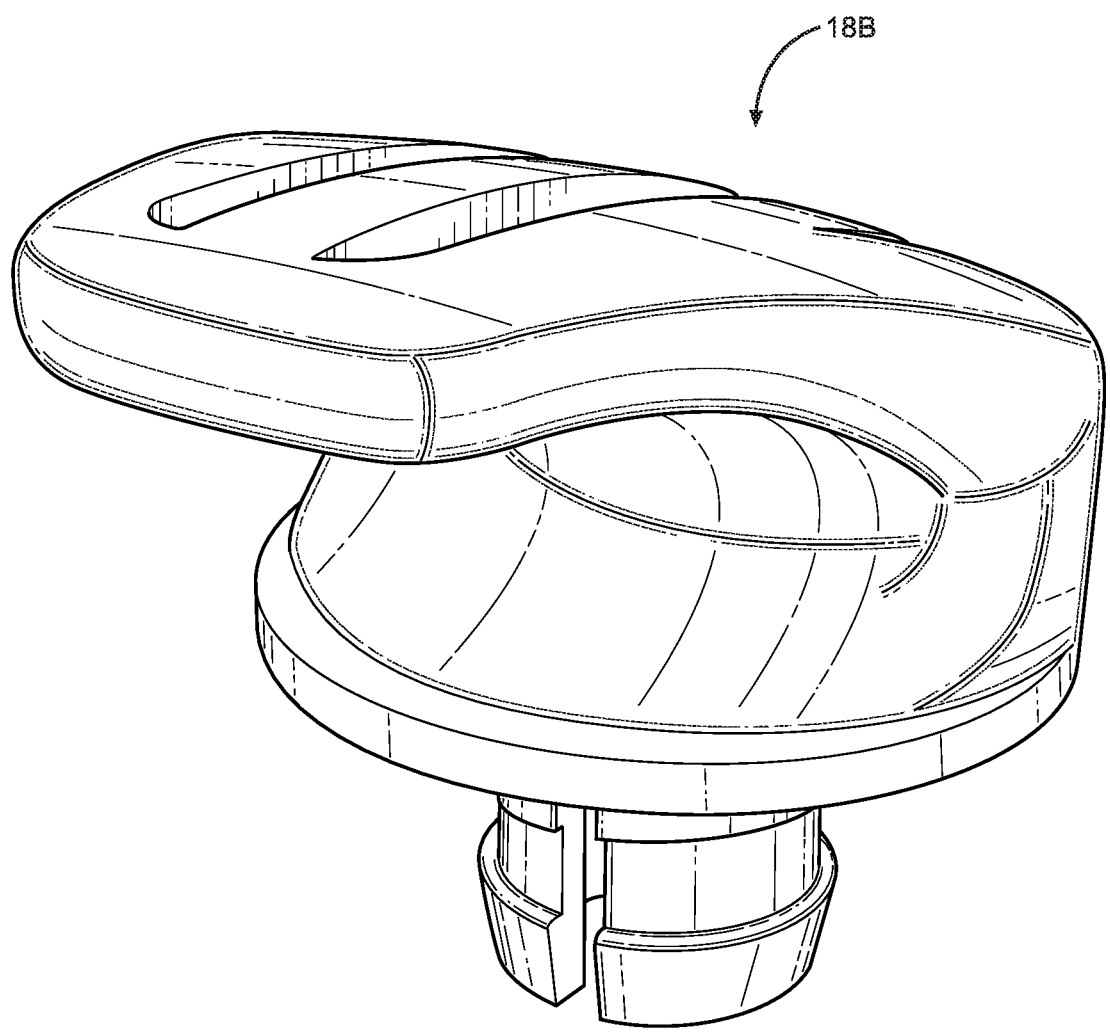
FIG. 16 shows a rotating hook component.

As seen in FIG. 15, the O-ring 20 is located within the handle 16a to press against the interior tube 18 to provide a seal to prevent procedure inflation gas from escaping during use of the system 10 in a surgical procedure. The handle 16a preferably defines an annular grove configured to receive the O-ring 20 and position the O-ring 20 to slidingly engage the interior tube 18. An additional seal 20a is also preferably located on the end of the outer cannula 16 for cooperating with the O-ring 20 to provide additional sealing characteristics. The seal 20a may be a heat shrinkinkable tube slipped over the end of the outer cannula 16 prior to mounting of the handle 16a. About half of the length of the heat shrinkable tube is heat shrunk onto the end of the cannula 16, and the remaining portion folded inside the cannula 16 as shown in FIG. 15.

The string 22 allows the user to cinch the basket 12b of the bag 12 closed after the tissue is placed inside the bag 12 and before the basket 12b and tissue are retrieved. Cinching of the basket 12b is depicted in FIG. 8. The string 22 is provided as a loop 22a, with a slip knot 22b. When the string 22 is pulled to cinch the basket 12b closed, the slip knot 22b serves to retain the basket 12b in the closed orientation. As used herein, the term string is intended to designate an elongate and thin flexible member having the characteristics of string. It will be appreciated that the term string encompasses other elongate, thin and flexible members such as ribbons, cords, lines, cables and the like. As seen in FIG. 9, after the basket 12b is cinched and the outer cannula 16 is removed, the bag 12 may be removed through the trocar cannula TC.

Figure 10:
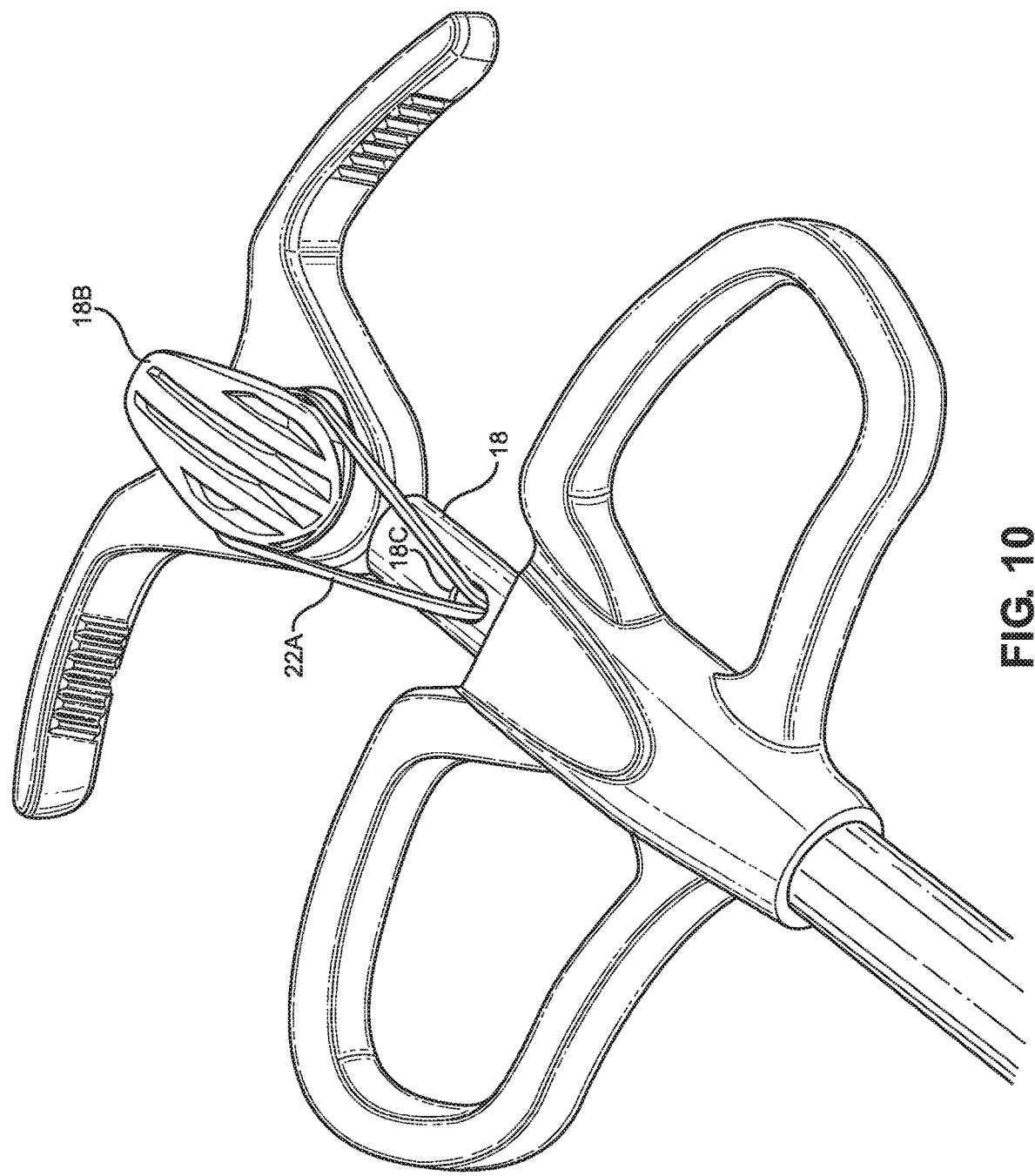
FIGS. 10 and 11 depict cooperation of a rotating hook component of the interior tube with a cinch string of the bag component.
Figure 11:
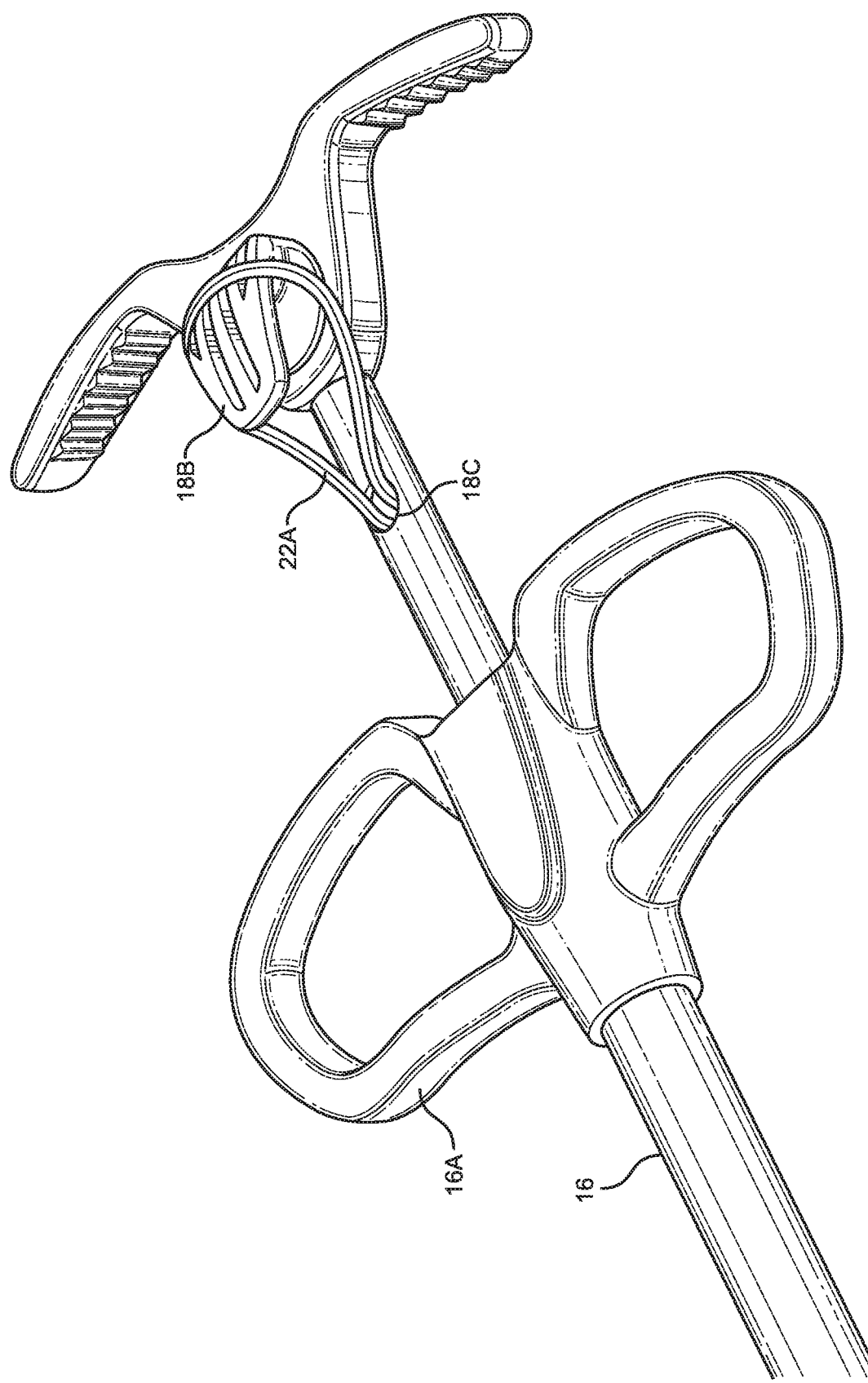
Figure 12:
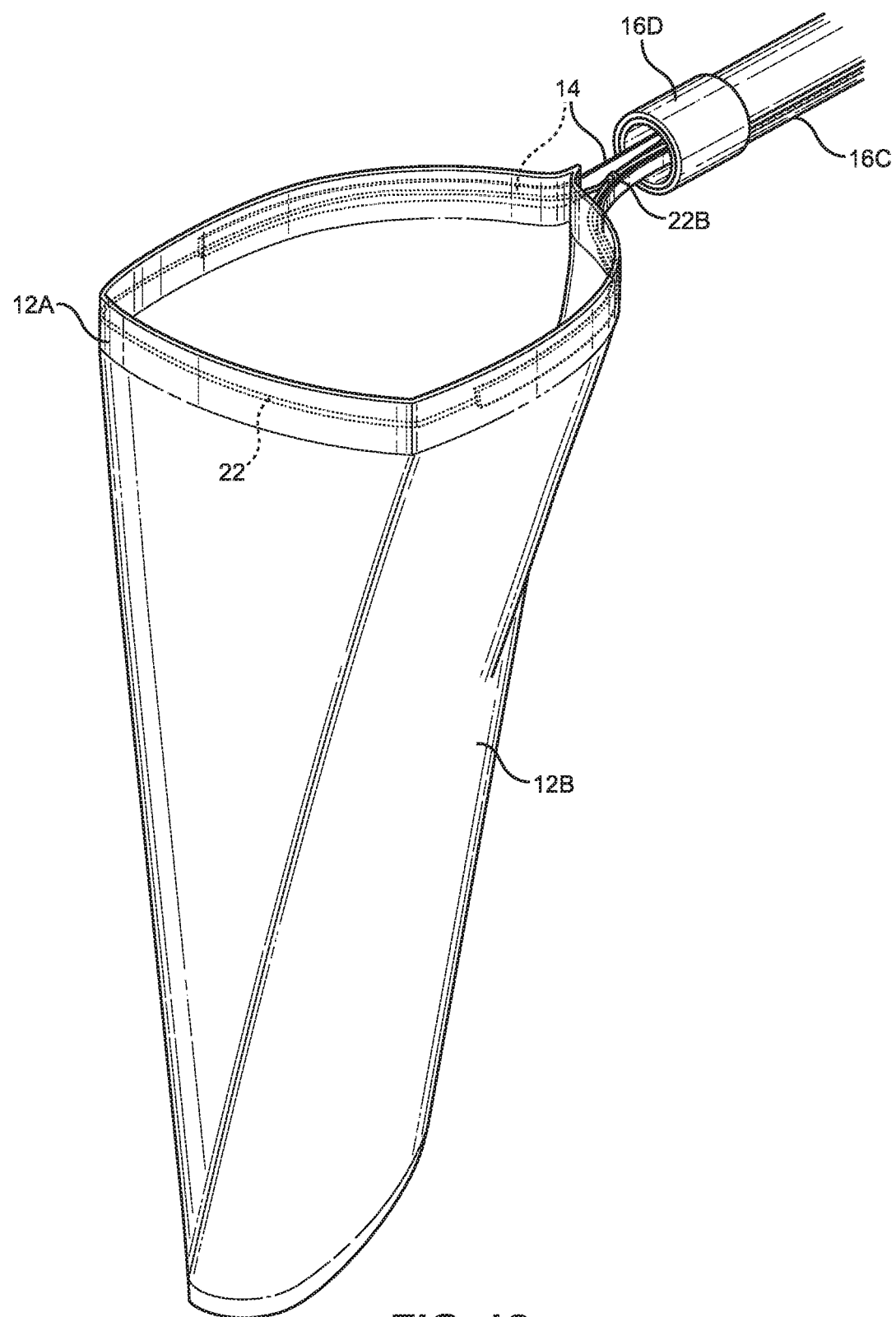
FIG. 12 is a close-up view of the bag component in the deployed state.
Figure 13:
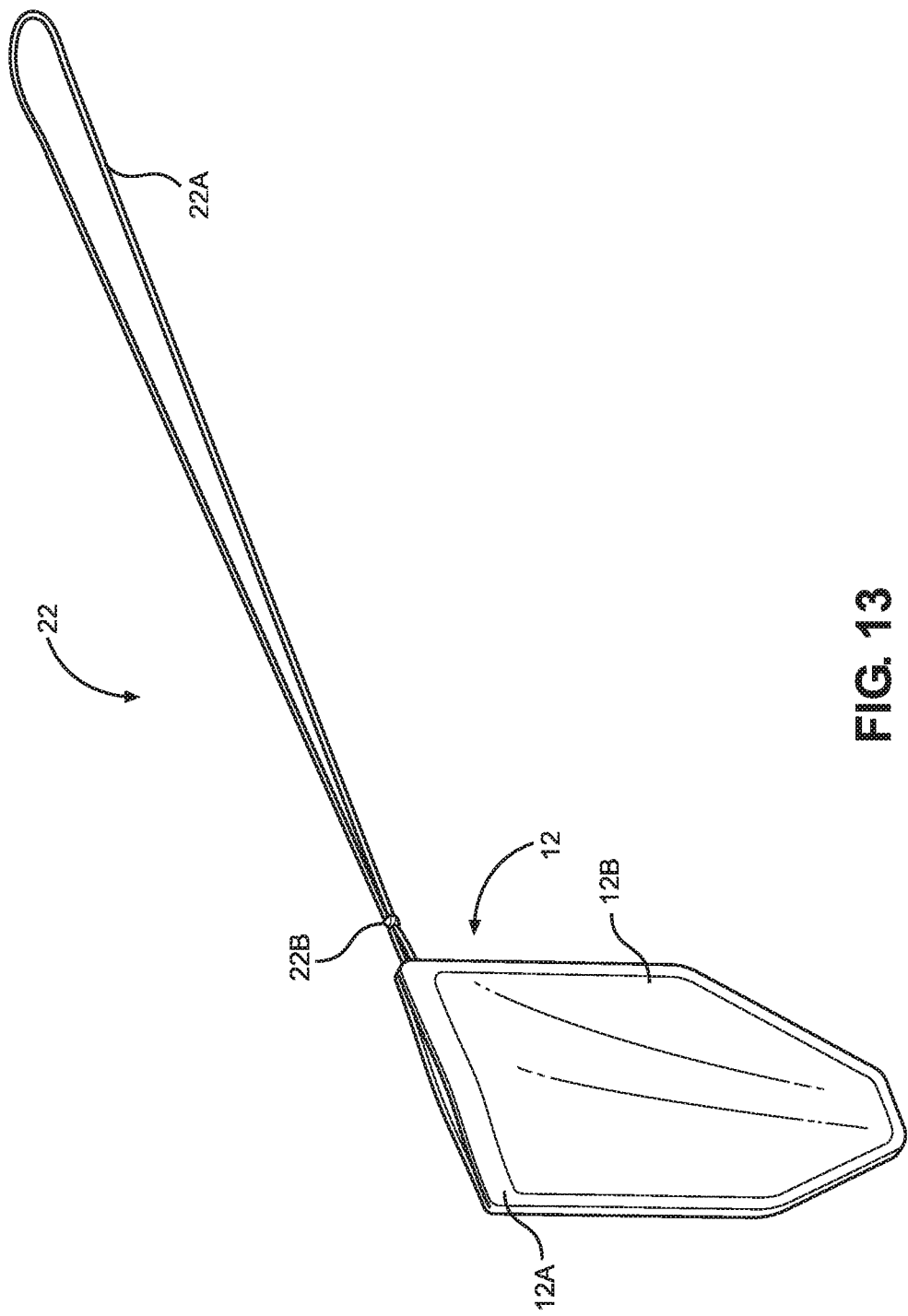
FIG. 13 shows the bag component having a cinch string.
Figure 17:
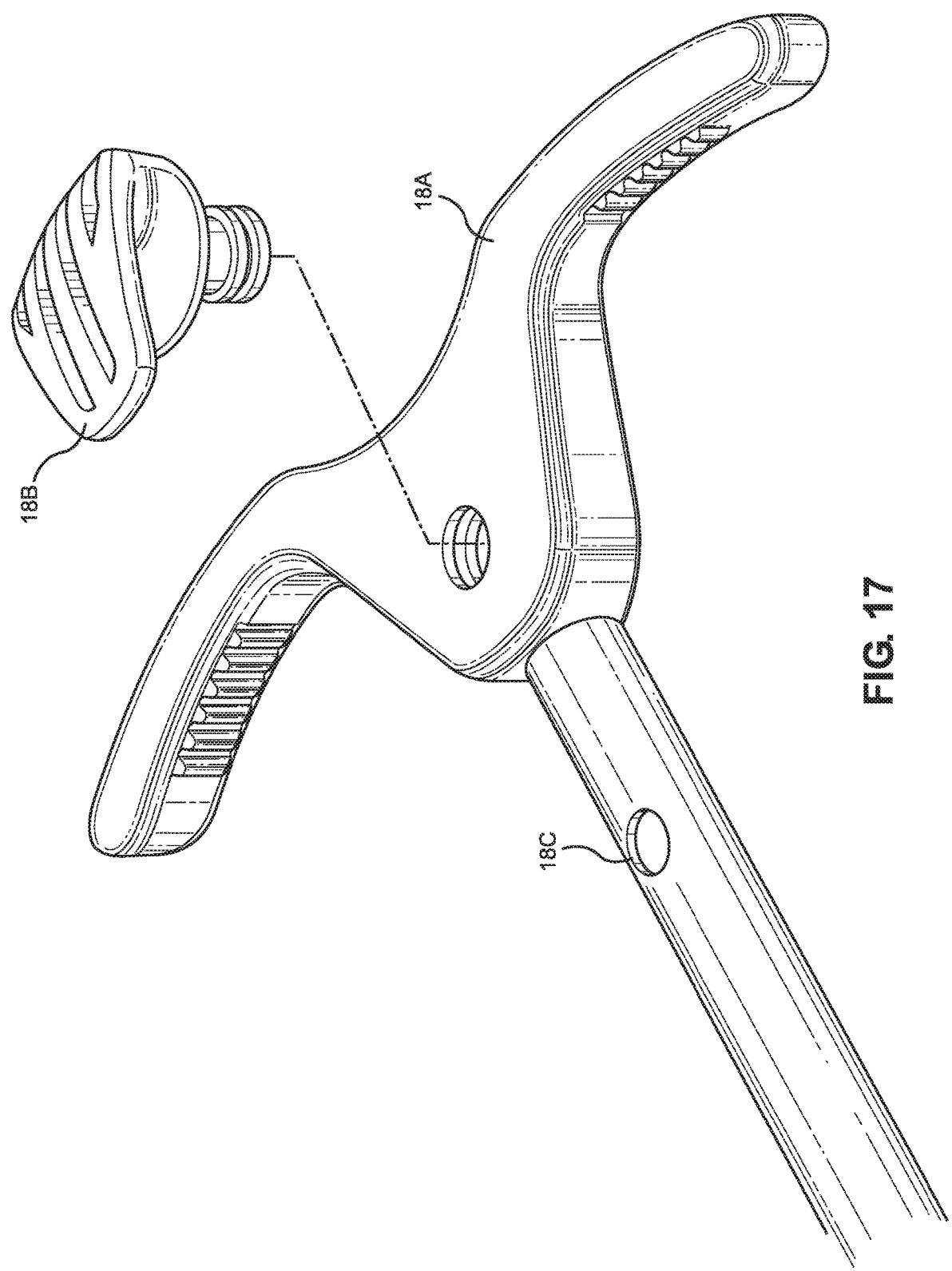
FIG. 17 is an exploded view showing the rotating hook component relative to a handle of the interior tube onto which the hook is rotatably installed.
Figure 18:
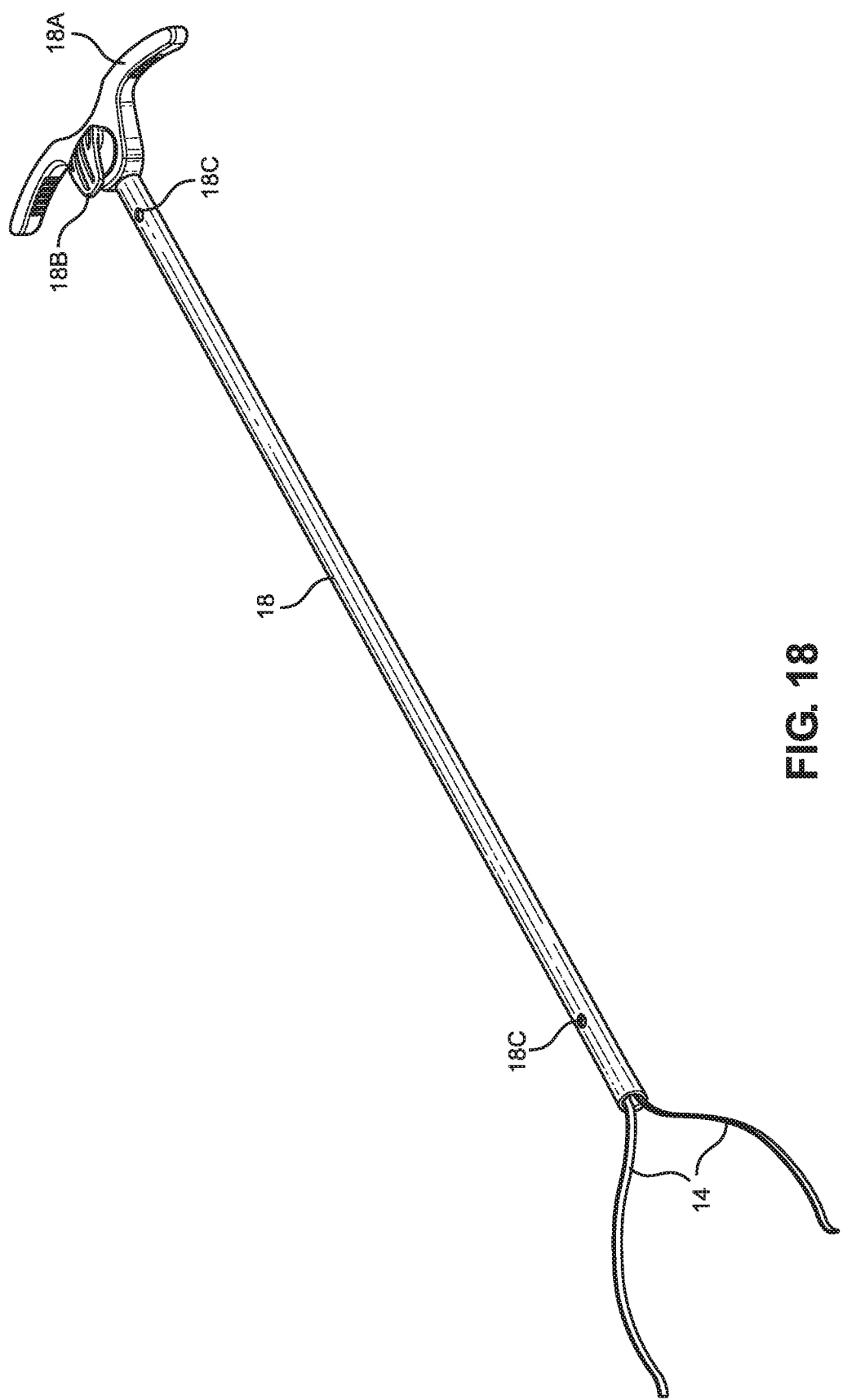
FIG. 18 shows the interior tube component.

The free or distal end of the loop 22a of the string 22 is securable to a rotatable hook 18b located on the handle 18a. The hook 18b preferably has a foot that snap fits into an aperture of the handle 18a to rotatably mount the hook 18b to the handle 18a (FIG. 17). As seen FIGS. 10 and 11, when the hook 18b is rotated from an upward position to a downward position, the loop 22a of the string 22 is able to slide off of and disengage from the hook 18b.

Figure 2:
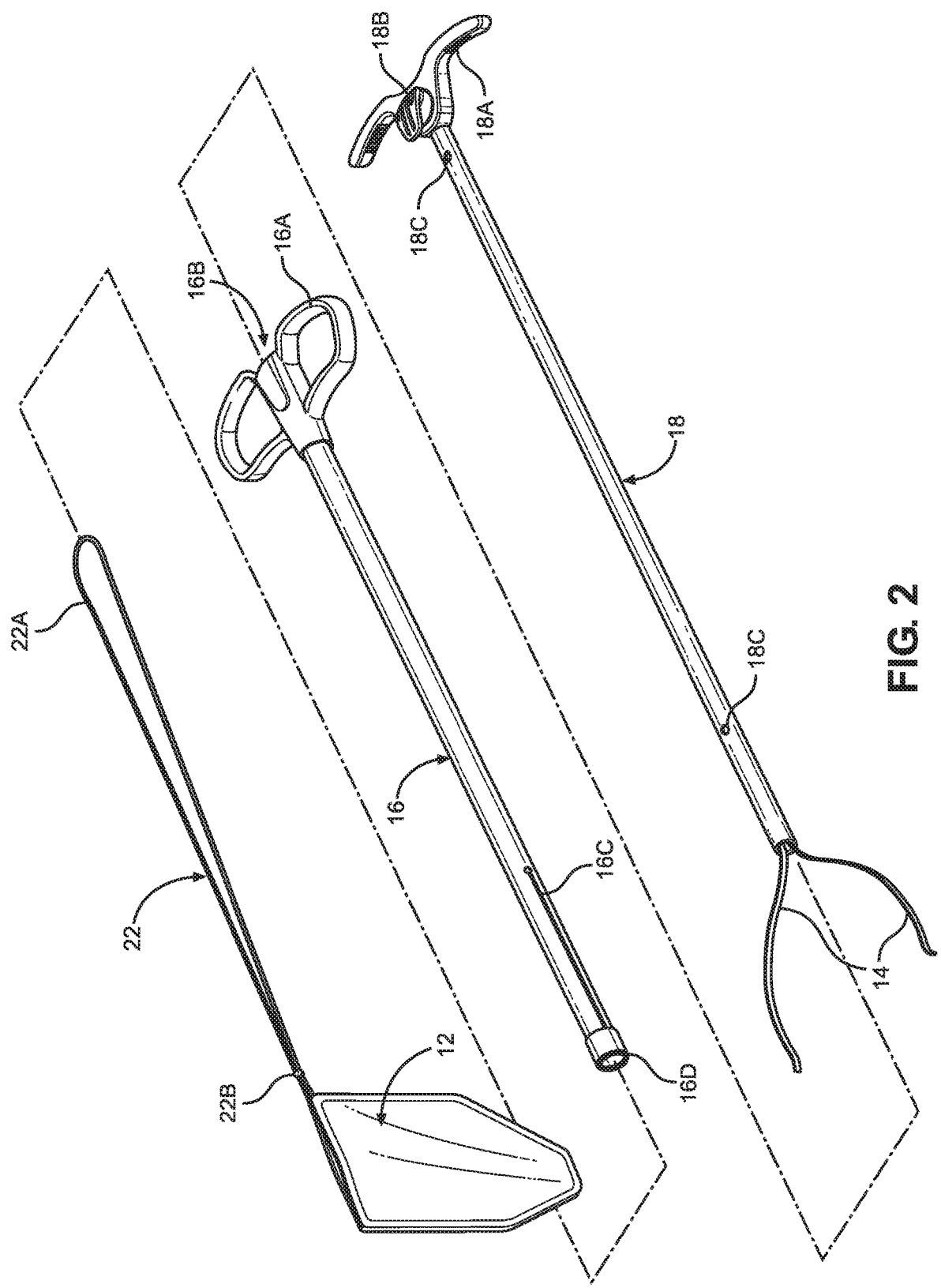
FIG. 2 is an exploded perspective view of the specimen retrieval system.

The string 22 and the distal end of the loop 22a extend through apertures 18c defined adjacent opposite ends of the interior tube 18 (FIG. 2). As seen in FIGS. 4 and 8, for the initial state of the system 10 and during deployment and retrieval of the bag 12, the string 12 is within the interior tube 18 between the apertures 18c, and with the distal end of the loop 22a secured to the upwardly oriented hook 18b.

With reference to FIGS. 7-9, after the basket 12b is deployed inside the body, the user will place the compromised tissue inside the basket 12b. Once the tissue is inside the basket 12b, the user will retract the interior tube 18 and then remove the interior tube 18. Following this, the basket 12b will be cinched closed using the string 22 (FIG. 8). As depicted in FIG. 9, the outer cannula 16 is then removed, and the cinched bag 12 may be pulled through the trocar cannula TC and removed from the incision site.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. A specimen retrieval system, comprising:
a bag having a flexible basket with an opening configured to be deployable for receiving a tissue specimen, and an elongate string encircling the flexible basket and extending therefrom to terminate remote from the flexible basket, the string being operable to close the opening of the flexible basket;
an outer cannula having a distal end and a proximal end with a cannula handle located at the proximal end of the outer cannula, the outer cannula having a lumen configured to receive the bag therein and to permit passage of the bag through the distal end of the outer cannula for deployment of the bag, the outer cannula further including an elongate slit adjacent the distal end of the outer cannula configured for enabling positioning of the flexible basket through the slit and for retrieval of the flexible basket through the slit for positioning of the bag within the outer cannula; and
an interior tube having a distal end slidably positionable within the outer cannula via the proximal end of the outer cannula, the interior tube having a tube handle mounted to a proximal end of the interior tube at a location exterior of the cannula handle, a distal aperture defined on the interior tube proximal the distal end of the interior tube and a proximal aperture defined on the interior tube distal the proximal end of the interior tube, the distal and proximal apertures configured for passage of the string into the interior tube via the distal aperture and for passage of the string out of the interior tube via the proximal aperture, and a spring secured within the distal end of the interior tube and extending outwardly of the distal end of the interior tube, the spring connectable to the opening of the basket of the bag.

2. The system of claim 1, further comprising a seal located within the cannula handle to contact the interior tube to provide a seal.

3. The system of claim 1, wherein the cannula handle defines an annular groove configured to receive an O-ring to contact the interior tube and provide a seal.

4. The system of claim 1, wherein the string includes a slip knot adjacent the flexible basket.

5. The system of claim 1, wherein the string is configured as a loop, the loop being configured to pass through the distal aperture and the proximal aperture.

6. The system of claim 1, the tube handle including a hook rotatably mounted thereon and configured for engaging the loop of the string when rotated to a first position and configured for disengaging from the loop when rotated to a second position.

7. The system of claim 1, wherein the spring comprises a pair of flat springs.

8. A specimen retrieval system, comprising:
a bag having a flexible basket with an opening configured to be deployable for receiving a tissue specimen, and an elongate string encircling the flexible basket and extending therefrom to terminate remote from the flexible basket, the string being operable to close the opening of the flexible basket;
an outer cannula having a distal end and a proximal end with a cannula handle located at the proximal end of the outer cannula, the outer cannula having a lumen configured to receive the bag therein and to permit passage of the bag through the distal end of the outer cannula for deployment of the bag; and
an interior tube having a distal end slidably positionable within the outer cannula via the proximal end of the outer cannula, the interior tube having a tube handle mounted to a proximal end of the interior tube at a location exterior of the cannula handle, a distal aperture defined on the interior tube proximal the distal end of the interior tube and a proximal aperture defined on the interior tube distal the proximal end of the interior tube, the distal and proximal apertures configured for passage of the string into the interior tube via the distal aperture and for passage of the string out of the interior tube via the proximal aperture, and a spring secured within the distal end of the interior tube and extending outwardly of the distal end of the interior tube, the spring connectable to the opening of the basket of the bag.

\* \* \* \* \*